United States Patent [19]
Hattori et al.

[11] Patent Number: 5,053,229
[45] Date of Patent: Oct. 1, 1991

[54] COSMETIC COMPOSITIONS

[75] Inventors: Michihiro Hattori, Utsunomiya; Shuichi Akazaki, Ichikai; Naonobu Yoshizuka, Funabashi; Genji Imokawa, Utsunomiya, all of Japan

[73] Assignee: Kao Corporation, Tokyo, Japan

[21] Appl. No.: 300,217

[22] Filed: Jan. 24, 1989

Related U.S. Application Data

[63] Continuation of Ser. No. 875,683, Jun. 18, 1986, abandoned.

[30] Foreign Application Priority Data

Jul. 31, 1985 [JP] Japan .................. 60-169514

[51] Int. Cl.$^5$ .................. A61K 35/36; A61K 31/685; A61K 31/59; A61K 31/20
[52] U.S. Cl. .................. 424/572; 424/574; 514/78; 514/182; 514/558; 514/559; 514/560
[58] Field of Search .................. 424/95; 514/78, 182, 514/558–560, 572, 574

[56] References Cited

U.S. PATENT DOCUMENTS

| | | | |
|---|---|---|---|
| 3,660,566 | 5/1972 | Vinson et al. | 424/95 |
| 4,425,329 | 1/1984 | Tsutsumi et al. | 514/772 |
| 4,457,910 | 7/1984 | Van Cleave | 424/59 |
| 4,634,719 | 1/1987 | Takaishi et al. | 514/772 |

OTHER PUBLICATIONS

Strianse, in Cosmetics: Science and Technology, vol. 1, Chapter 5 (1972), pp. 179–181, 187–188, 216–217.
Lampe et al., Chem. Abstracts, vol. 98:158452g (1983).

Primary Examiner—Jacqueline Stone
Attorney, Agent, or Firm—Oblon, Spivak, McClelland, Maier & Neustadt

[57] ABSTRACT

Novel cosmetic compositions comprising a lipid derived from horny cells can enhance a moisture retention ability of the horny layer and are useful for remedy of dry skin. When the lipid is used in combination with surface active agents, the above effect is enhanced.

The cosmetic compositions may take any preparations such as creams, milky lotions, beauty wash, rouges, foundations, hair tonics and the like.

8 Claims, 1 Drawing Sheet

COSMETIC COMPOSITIONS

This application is a continuation of application Ser. No. 06/875,683, filed on June 18, 1986, now abandoned.

BACKGROUND OF THE INVENTION

1) Field of the Invention

This invention relates to novel cosmetic compositions and more particularly, to cosmetic compositions which can enhance a moisture retention ability of the horny layer and are useful for remedy of dry skin.

2) Description of the Prior Art

It is known that in order to impart moistness to the skin and make the skin soft, the content of moisture in the horny layer is important. The retention of the moisture or water is considered to rely on water-soluble components in the horny layer, such as free amino acids, organic acids, urea, inorganic ions and the like. These substances are formulated in cosmetic compositions singly or in combination in order to keep or prevent the skin from chapping. Alternatively, a number of humectants which have high affinity for water have been developed and are used for similar purposes.

However, when applied to the skin, these humectant substances serve to supply moisture to the horny layer on the surface of the skin, with the effect being temporary. In other words, these substances do not fundamentally improve the moisture retention in the horny layer and do not thus substantially remedy dry skin.

SUMMARY OF THE INVENTION

Under these circumstances in the art, the present inventor made intensive studies to solve the above problems. As a result, it was found that a lipid obtained from horny cells (hereinafter referred to as horny cell-derived lipid) had the capability of fundamentally improving the moisture retention in the horny layer. Moreover, when the lipid was used in combination with surface active agents, the effect was found to increase. The present invention was accomplished on the basis of the above findings.

According to the invention, there are provided cosmetic compositions which comprise a horny cell-derived lipid with or without surface active agents.

BRIEF DESCRIPTION OF THE DRAWING

The sole FIGURE is a graph of a skin scaling score in relation to the number of days during which cosmetic compositions are used.

DETAILED DESCRIPTION OF THE INVENTION AND PREFERRED EMBODIMENTS

Figure 1:
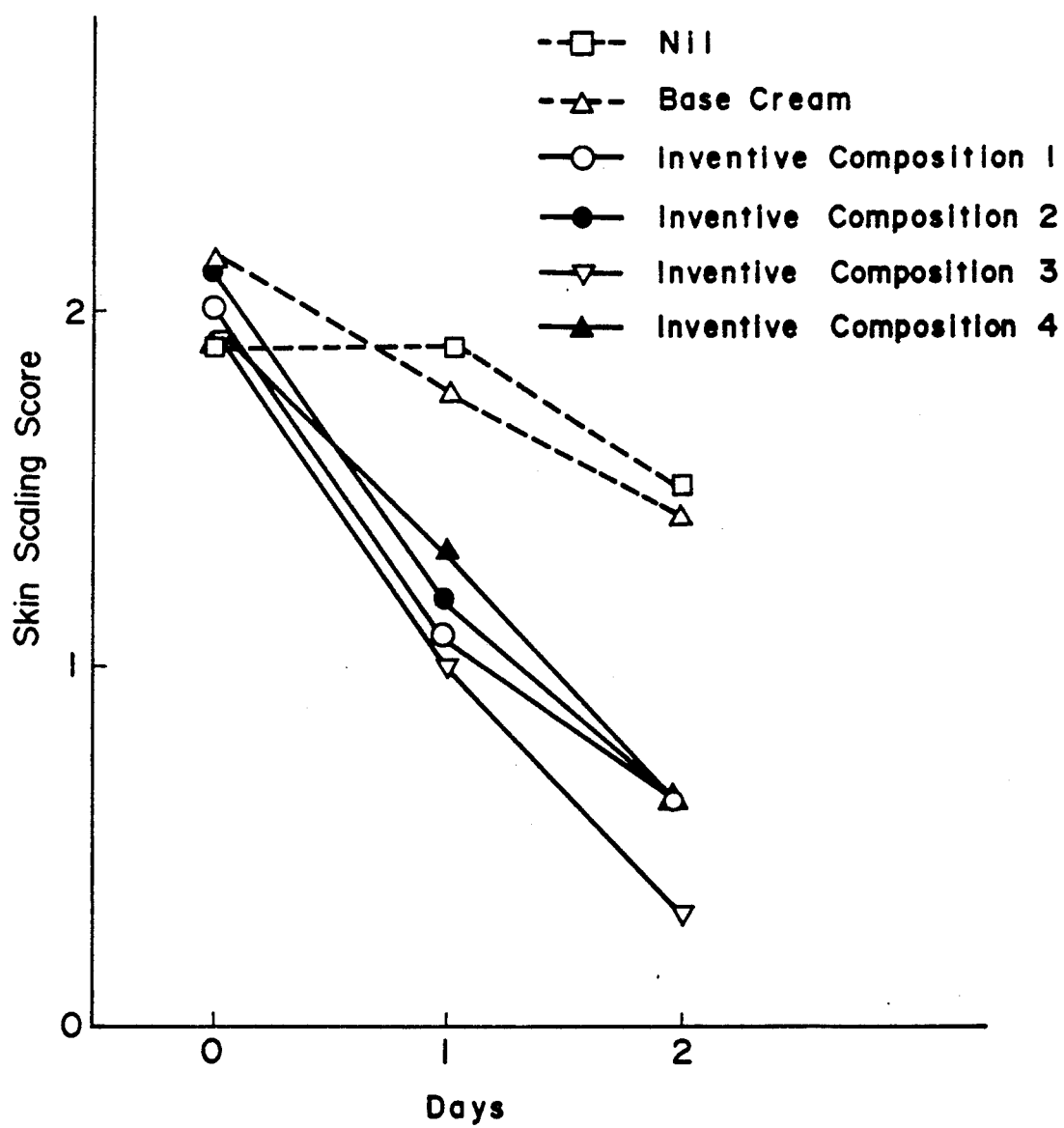

The horny cell-derived lipid used in the present invention is obtained, for example, by extracting horny cells of mammals with organic solvents.

The horny cells may be those cells of mammals such as man, pig, cattle, horse, sheep, goat, mouse, rat, rabbit, dog, guinea pig, cat, monkey and the like.

The horny cells are first subjected to preliminary extraction to remove lipids derived from the sebaceous gland such as triglycerides, squalene, waxes and the like and then, a horny cell-derived lipid is extracted.

For the preliminary extraction, there may be used such solvents as used for the extraction of the horny cell-derived lipid, e.g. chloroform, ethanol, acetone, ethyl ether and the like. The preliminary extraction is effected as follows: horny cells are immersed in a solvent as indicated above within a short time of, for example, 30 seconds to 10 minutes. By this, the lipids derived from the sebaceous gland are removed.

For the extraction of the horny cell-derived lipid, the horny cells after the preliminary extraction are immersed in a solvent such as, for example, chloroform, ethanol, methanol, ethyl ether, acetone, benzene, hexane or a mixture thereof. The extract is conducted at a temperature of from 5° to 40° C. for 1 minute or more, preferably from 2 to 5 hours.

The thus obtained horny cell-derived lipid may be used after fractionation into individual components. For the fractionation, column chromatography, separative thin layer chromatography and the like are used. For instance, after preliminary extraction of horny cells with a mixed solvent of acetone and ether, the cells are extracted with the same mixed solvent as used above to collect a horny cell-derived lipid. The thus collected lipid is subjected to silica gel column chromatography, followed by elution with ethyl ether/petroleum ether (1/99) (fraction 1), ethyl ether/petroleum ether (25/75) (fraction 2), ethyl ether (fraction 3), and ethanol (fraction 4) to collect the respective fractions. The constituent components of the horny cell-derived lipid have not yet completely been isolated and identified, but it has been confirmed that fraction 1 is mainly composed of a cholesterol ester, fraction 2 is mainly composed of a free fatty acid, fraction 3 is mainly composed of a glycolipid and a sphingolipid, and fraction 4 is mainly composed of a phospholipid. Of these fractions, fractions 3 and 4 are preferred, of which fraction 3 is most preferable in the practice of the invention.

The amount of the horny cell-derived lipid in cosmetic compositions is not critical, and is generally in the range of 0.001 to 50 wt % (hereinafter referred to as %), preferably from 0.1 to 20%, of the total composition for emulsion cosmetics, and is from 1 to 50%, preferably from 5 to 25%, for oil-type cosmetics using liquid hydrocarbon bases such as squalene.

The surface active agents may be nonionic surface active agents, anionic surface active agents, and amphoteric surface active agents. Preferably, there are used alkali metal salts or basic amino acid salts of monoalkyl or alkenyl (having from 8 to 22 carbon atoms) phosphates, and nonionic surface active agents.

Examples of the nonionic surface active agents include polyoxyethylene alkyl ethers, polyoxyethylene alkylphenyl ethers, polyoxyethylene fatty acid esters, sorbitan fatty acid esters, polyoxyethylene sorbitan fatty acid esters, fatty acid monoglycerides, glyceryl ethers, and the like. Of these, there are preferably used glyceryl ethers of the general formula (I)

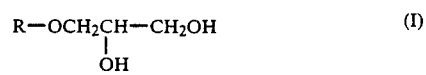

in which R represents an alkyl group having from 8 to 24 carbon atoms. Of the alkyl groups represented by R, an alkyl group of the formula (II) is preferred

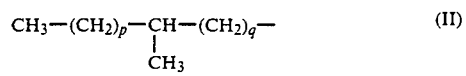

in which p is an integer of from 4 to 10, q is an integer of from 5 to 11, and $p+q=11$ to 17 with a distribution having an apex at $p=7$ and $q=8$.

The amount of the surface active agent is from 0.01 to 20%, preferably from 0.1 to 5%, of the total composition.

The cosmetic compositions of the invention may further comprise, aside from the above essential ingredients, oils, humectants, UV absorbers, alcohols, chelating agents, pH adjustors, preservatives, thickeners, colorants, perfumes or mixtures thereof.

The cosmetic compositions may take any preparations including, for example, W/O and O/W emulsion cosmetics, creams, milky lotions, beauty wash, oil-type cosmetics, rouges, foundations, and other skin cosmetics such as skin detergents, hair tonics, hair dressers, hair growers and the like.

Although the action mechanism of the horny cell-derived lipid in the cosmetic compositions has not completely been made clear, it is believed that the lipid serves to reconstruct the lipid membrane between horny cells and thus, shows the moisture retentive function.

As described hereinabove, the cosmetic compositions of the invention in which the horny cell-derived lipid is formulated can remedy and prevent dry skin.

The present invention is described by way of examples and references.

REFERENCE 1

Preparation of Horny Cell-Derived Lipid

One hundred grams of human horny cells was preliminarily extracted with a mixed solvent (25° C.) of acetone and ethyl ether (ratio by volume of 1:1) for 10 minutes, after which it was extracted with a similar mixed solvent for 20 minutes and the solvent was distilled off to obtain 752 mg of a horny cell-derived lipid.

The lipid was dissolved in a small amount of a mixed solvent of acetone and ethyl ether as used above and subjected to column chromatography using 100 g of silica gel. A fraction of elution with ethyl ether/petroleum ether (1/99) was collected as fraction 1 in an amount of 53 mg. Subsequently, ethyl ether/petroleum ether (25/75) was used for elution to obtain 42 mg of fraction 2, ethyl ether was used for elution to obtain 130 mg of fraction 3, and methanol was used for elution to obtain 100 mg of fraction 4.

The skin conductance and the skin scaling score in the following examples were measured or determined according to the following procedures unless described otherwise.

Test Methods

Forty 20 to 40 year-old females who have chapped cheeks in winter were chosen as a subject. Different cosmetics are applied to the left and right cheek of each of the subjects, respectively, for two weeks continuously. On the following day of two week applications, the skin condition was examined as follows.

(i) Skin Conductance

The face was washed with hot water of 37° C., followed by a rest for 20 minutes in a room of a temperature of 20° C. and a humidity of 40%. The moisture content in the horny layer was measured by a skin conductance meter (by IBS Co., Ltd.)

A smaller conductance value, especially less than 5 means a higher degree of skin dryness. If the value exceeds 20, little dryness is recognized.

(ii) Skin-scaling Score

The degree of the scaling was visually observed and evaluated according to the following standard.

| Score | Degree of roughness |
| --- | --- |
| 0 | no scaling |
| 1 | slight degree of scaling |
| 2 | scaling observed |
| 3 | medium degree of scaling |
| 4 | considerable degree of scaling |

EXAMPLE 1

A 3:1 mixture of vaseline and horny cell-derived lipid (fraction 3 obtained in Reference 1) (product of the invention), and vaseline were, respectively, applied onto the right or left cheek, followed by measurement of the skin conductance and evaluation of the skin scaling.

TABLE 1

|  | Inventive Product 1 | Vaseline |
| --- | --- | --- |
| skin conductance | 22 ± 6 | 7 ± 5 |
| scaling score | 1.0 ± 0.4 | 2.2 ± 1.5 |

EXAMPLE 2

The horny cell-derived lipids obtained in Reference 1 (fractions 1–4) were used to prepare W/O emulsion cosmetic compositions of the formulations indicated in Table 2. The cosmetic compositions were evaluated with regard to the scaling score. The evaluation was started simultaneously with the application of the respective cosmetic compositions. The results are shown in the sole FIGURE.

TABLE 2

| | | (wt %) | | | |
| --- | --- | --- | --- | --- | --- |
| | | Cosmetic Compositions of Invention | | | |
| Composition | Base Cream | 1 | 2 | 3 | 4 |
| Glyceryl ether (I) [in formula (I), R is of the formula (II)] | 2.0 | 2.0 | 2.0 | 2.0 | 2.0 |
| 2-Octyldodecyl myristate | 10.0 | 10.0 | 10.0 | 10.0 | 10.0 |
| Vaseline | 3.0 | 3.0 | 3.0 | 3.0 | 3.0 |
| Squalane | 5.0 | 5.0 | 5.0 | 5.0 | 5.0 |
| Tocopheryl acetate | 0.5 | 0.5 | 0.5 | 0.5 | 0.5 |
| Horny cell-derived lipid | | | | | |
| fraction 1 | | 1.0 | | | |

TABLE 2-continued

|  | Base Cream | Cosmetic Compositions of Invention | | | |
|---|---|---|---|---|---|
| Composition |  | 1 | 2 | 3 | 4 |
| fraction 2 |  |  | 1.0 |  |  |
| fraction 3 |  |  |  | 1.0 |  |
| fraction 4 |  |  |  |  | 1.0 |
| Water | balance | balance | balance | balance | balance |

EXAMPLE 3

Cosmetic compositions indicated in Table 3 were prepared and were, respectively, applied to the left and right cheek of each of ten 20 to 40 year-old females once a day, who have dry cheeks in winter. Two weeks after the application, the skin conductors and the scaling score were evaluated according to the test methods described before. The results are shown in Table 3.

TABLE 3

|  | (wt %) | |
|---|---|---|
|  | Inventive Product 6 | Inventive Product 7 |
| Horny cell-derived lipid (fraction 3 obtained in Reference 1) | 2 | 2 |
| Glyceryl ether (I) (as used in Example 2) | 0 | 1 |
| Squalene | 98 | 97 |
| Evaluation: |  |  |
| Skin conductance | 15 ± 5 | 24 ± 5 |
| Scaling score | 1.2 ± 0.5 | 0.3 ± 0.3 |

As will be apparent from the above results, the horny cell-derived lipid enhances the moisture retaining ability of the horny layer and can prevent the skin from dryness. These effects are more improved when the lipid is used in combination with surface active agents rather than used singly.

What is claimed is:

1. A cosmetic composition, consisting essentially of:
   (a) a lipid derived from horny cells, which is selected from the group consisting of:
      (1) a fraction substantially comprising a mixture of one or more sphingolipids and one or more glycolipids; and
      (2) a fraction substantially comprising one or more phospholipids, said lipid being present in an amount effective to enhance moisture retention of a horny layer of skin when applied thereto; and a mixture of any of the above; and
   (b) an effective amount of a surfactant consisting of the glyceryl ether of the formula:

$$R-OCH_2CH-CH_2OH$$
$$\phantom{R-OCH_2}|$$
$$\phantom{R-OCH_2}OH$$

wherein R is a $C_8$-$C_{24}$ alkyl group.

2. The cosmetic composition of claim 1, wherein R of the formula represents:

$$CH_3-(CH_2)_p-CH-(CH_2)_q-$$
$$\phantom{CH_3-(CH_2)_p-}|$$
$$\phantom{CH_3-(CH_2)_p-}CH_3$$

wherein p is an integer of from 4 to 10, q is an integer of from 5 to 11, and p+q has a value of 11 to 17 with a distribution apex of p=7 and q=8.

3. A cosmetic composition, consisting essentially of:
   (a) a lipid derived from horny cells, which is selected from the group consisting of:
      (1) a first fraction substantially comprising one or more cholesterol esters;
      (2) a second fraction substantially comprising one or more free fatty acids;
      (3) a third fraction substantially comprising a mixture of one or more sphingolipids and one or more glycolipids; and
      (4) a fourth fraction substantially comprising one or more phospholipids, said lipid being present in an amount effective to enhance moisture retention of a horny layer of skin when applied thereto; and a mixture of any of the above; and
   (b) an effective amount of a surfactant consisting of the glyceryl ether of the formula:

$$R-OCH_2CH-CH_2OH$$
$$\phantom{R-OCH_2}|$$
$$\phantom{R-OCH_2}OH$$

wherein R is a $C_8$-$C_{24}$ alkyl group.

4. The cosmetic composition of claim 3, wherein R of the formula represents:

$$CH_3-(CH_2)_p-CH-(CH_2)_q-$$
$$\phantom{CH_3-(CH_2)_p-}|$$
$$\phantom{CH_3-(CH_2)_p-}CH_3$$

wherein p is an integer of from 4-10, q is an integer of from 5-11, and p+q has a value of 11-17 with a distribution apex at p=7 and q=8.

5. The cosmetic composition of claim 3, which comprises from 0.1 to 20% of said glyceryl ether, based on the total composition.

6. The cosmetic composition of claim 5, which comprises from 0.1 to 5% of said glyceryl ether, based on the total composition.

7. The cosmetic composition of claim 1, which comprises from 0.01 to 20% of said glyceryl ether, based on the total composition.

8. The cosmetic composition of claim 7, which comprises from 0.1 to 5% of said glyceryl ether, based on the total composition.

* * * * *